United States Patent [19]

Erskine

[11] Patent Number: 5,507,728
[45] Date of Patent: Apr. 16, 1996

[54] PERISTALTIC INTERLUMENAR DEVICE ADVANCES

[76] Inventor: Timothy J. Erskine, 1904 Millcrest Ave., Salt Lake City, Utah 84109

[21] Appl. No.: 343,282

[22] Filed: Nov. 22, 1994

Related U.S. Application Data

[63] Continuation of Ser. No. 129,221, Sep. 30, 1993, abandoned.

[51] Int. Cl.$^6$ .................................................. A61M 5/178
[52] U.S. Cl. ................................... 604/164; 604/159
[58] Field of Search ............................ 604/158, 159, 604/164, 170, 171

[56] References Cited

U.S. PATENT DOCUMENTS

| | | | |
|---|---|---|---|
| Re. 34,086 | 10/1992 | George | 128/200.26 |
| 3,000,380 | 9/1961 | Doherty | 128/214 |
| 3,416,531 | 12/1968 | Edwards | 128/348 |
| 3,515,137 | 6/1970 | Santomieri | 128/214.4 |
| 3,570,485 | 3/1971 | Kelly | 128/214.4 |
| 3,595,230 | 7/1971 | Suyeeka | 128/214.4 |
| 3,682,173 | 8/1972 | Center | 128/214.4 |
| 3,703,174 | 11/1972 | Smith | 128/214.4 |
| 3,757,771 | 9/1973 | Ruegg et al. | 128/2.1 |
| 3,835,854 | 9/1974 | Jewett | 128/214.4 |
| 3,903,885 | 9/1975 | Fuchs | 128/214.4 |
| 4,068,659 | 1/1978 | Moorehead | 604/159 |
| 4,205,675 | 6/1980 | Vaillancourt | 128/214.4 |
| 4,243,034 | 1/1981 | Brandt | 128/214.4 |
| 4,326,520 | 4/1982 | Alley | 128/214.4 |
| 4,417,886 | 11/1983 | Frankhouser et al. | 604/53 |
| 4,525,157 | 6/1985 | Vaillancourt | 604/168 |
| 4,652,256 | 3/1987 | Vaillancourt | 604/171 |
| 4,772,264 | 9/1988 | Cragg | 604/158 |
| 4,834,710 | 5/1989 | Fleck | 604/171 |
| 4,850,983 | 7/1989 | Brenneman et al. | 604/170 |
| 4,976,697 | 12/1990 | Walder et al. | 604/164 |
| 5,064,415 | 11/1991 | Walder et al. | 604/164 |
| 5,137,517 | 8/1992 | Loney et al. | 604/159 |
| 5,158,544 | 10/1992 | Weinstein | 604/164 |
| 5,163,913 | 11/1992 | Rantanen-Lee et al. | 604/177 |
| 5,201,712 | 4/1993 | Bryant | 604/164 |
| 5,234,411 | 8/1993 | Valliancourt | 604/171 |

FOREIGN PATENT DOCUMENTS

| | | | |
|---|---|---|---|
| 0468316A2 | 1/1992 | European Pat. Off. | |
| 9101156 | 2/1991 | WIPO | 604/164 |

*Primary Examiner*—John G. Weiss

[57] ABSTRACT

A medical device for advancing or retracting an elongate member is disclosed. The device is made up of a flexible tube. The elongate member is connected to a bead. The bead and elongate member are disposed axially within the tube. An advancer is provided which squeezes the walls of the tube together around the bead. The elongate member is thus advanced or retracted in the tube. The bead is provided with grooves to facilitate the flow of fluid through the tube. The elongate object may be an obturator or a probe for detecting a physiological parameter. Also disclosed is a a method for advancing or retracting an elongate member. The method has the steps of connecting the elongate member to a bead-like object, enclosing the elongate member and the bead within a hollow flexible tube, squeezing the tube near the bead-like object and imparting a substantially axial force to the tube such that the force is transmitted to the bead, thereby advancing the bead and the elongate object axially along the tube.

25 Claims, 3 Drawing Sheets

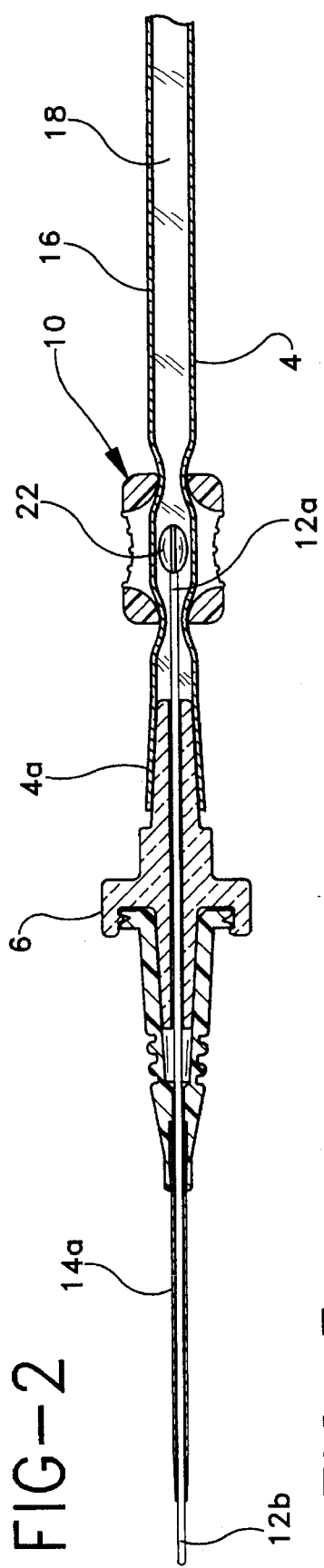
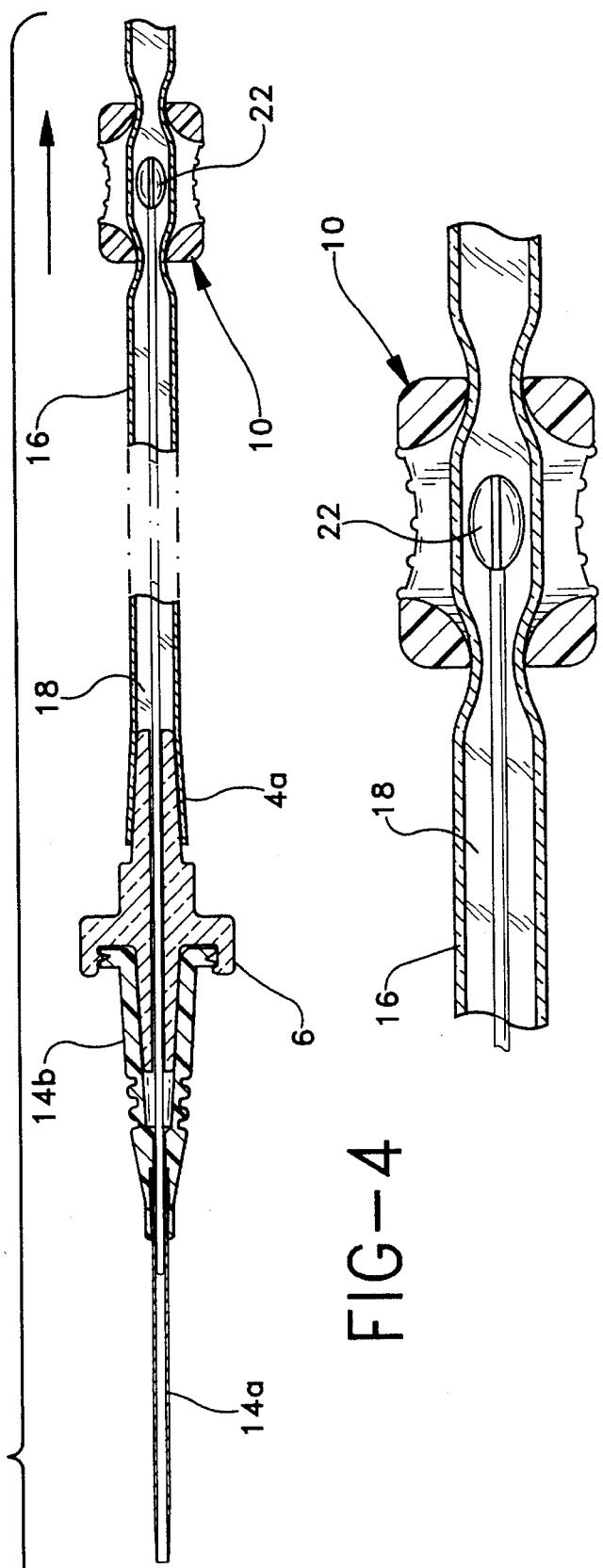
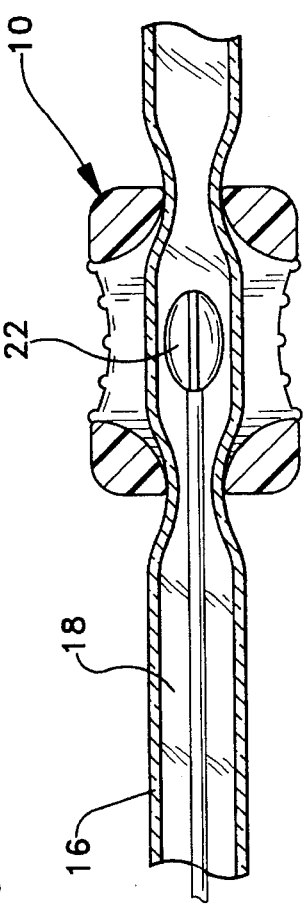

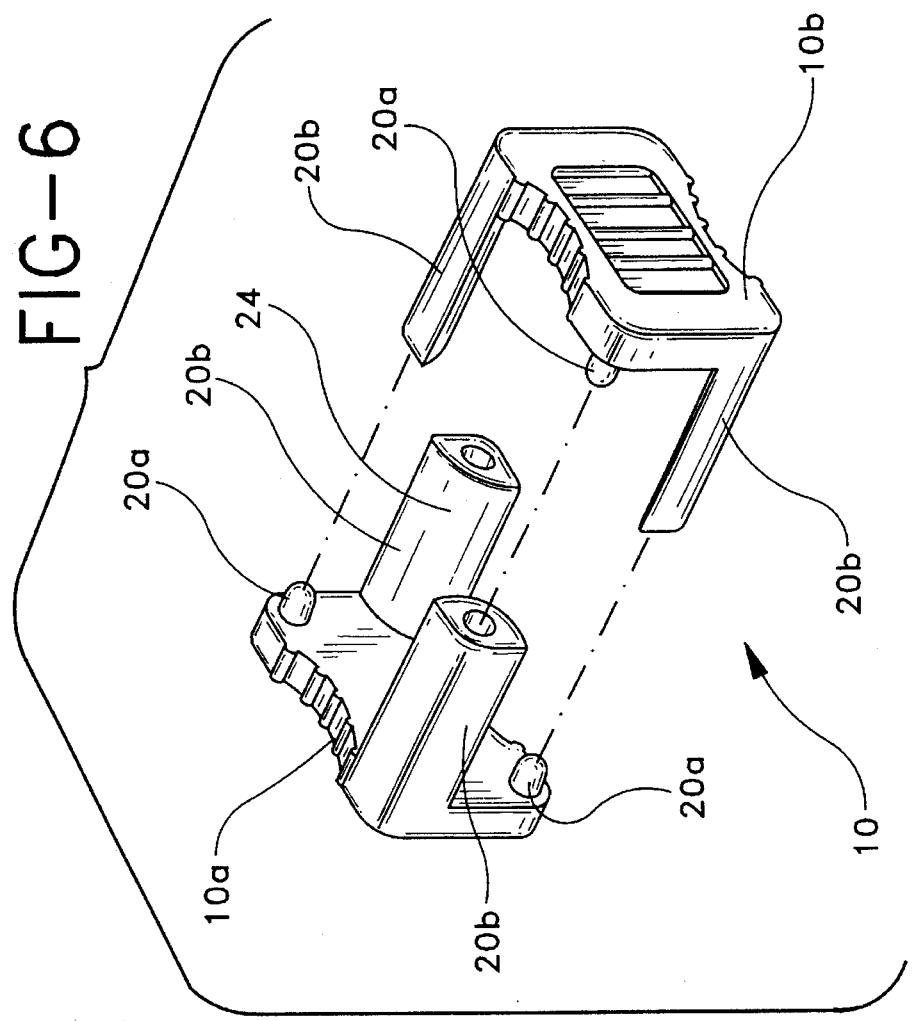
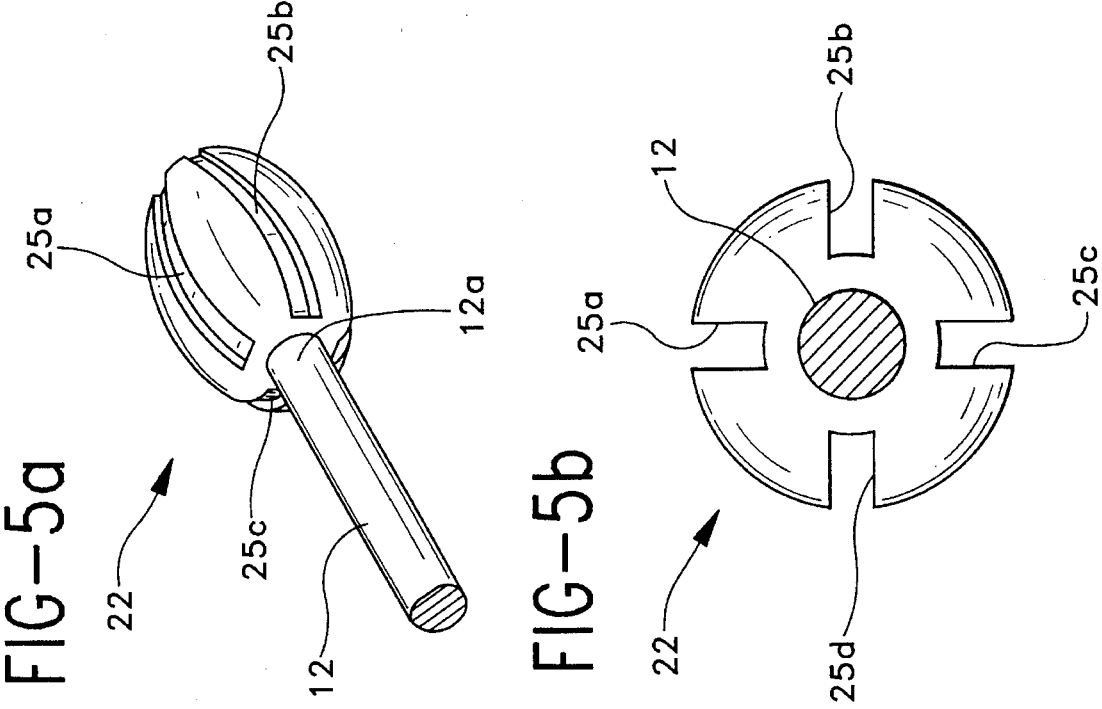

PERISTALTIC INTERLUMENAR DEVICE ADVANCES

This application is a continuation of application Ser. No. 08/129,221, filed Sep. 30, 1993 now abandoned.

BACKGROUND

The present invention relates to a device for advancing an object such as an obturator, a needle or a probe into the body via a catheter.

In the course of medical treatment it is often desirable to infuse fluids such as medications into, or withdraw fluids from a patient. This is typically accomplished by the introduction of a catheter into the patient in order to gain access to the vascular system of the patient. In such cases, it is sometimes desirable to occlude the catheter between successive infusions or withdrawals of fluid in order to maintain the patency of the catheter. Examples of devices for performing such an operation may be found in U.S. Pat. Nos. 5,201,712 and 4,976,697.

It has also become desirable to introduce certain therapeutic or measurement devices into the body via a catheter. For example, an invasive blood pressure sensor or blood gas sensor may be introduced into a blood vessel through a catheter.

The present invention is intended to provide a device for advancing an object such an obturator or probe into the body without exposing the object to infection.

SUMMARY OF THE INVENTION

The present invention relates to a device for advancing or retracting an elongate member through a catheter. The elongate member may be a device such as an obturator or a probe for detecting a physiological parameter. The device is made up of a flexible tube having a first end and a second end, a lumen and a flexible wall. The tube is dimensioned to accommodate the elongate object in the lumen. A connector is provided to connect the first end of the tube to a catheter. Secured to the elongate member is a bead-like object. An advancer is attached to the tube to impart force to the bead-like object, thereby causing the elongate member to move axially within the lumen.

The invention also includes a method for advancing or retracting an elongate member. The method has the steps of connecting the elongate member to a bead-like object, enclosing the elongate member and the bead within a hollow flexible tube, squeezing the tube near the bead-like object and imparting a substantially axial force to the tube such that the force is transmitted to the bead, thereby advancing the bead and the elongate object axially along the tube.

BRIEF DESCRIPTION OF THE DRAWINGS

FIG. 2 is a partial cross-sectional view through section 2—2 showing an obturator or probe in its advanced position;

FIG. 3 is a partial cross-sectional view through section 2—2 showing the obturator or probe in a retracted position;

FIG. 4 is a cross-sectional view through section 4—4 showing the device advancer in detail;

FIG. 5a is a perspective view of the bead-like object of the advancer;

FIG. 5b is an end view of the bead-like object; and

FIG. 6 is an exploded view of the advancer.

DETAILED DESCRIPTION

Figure 1:
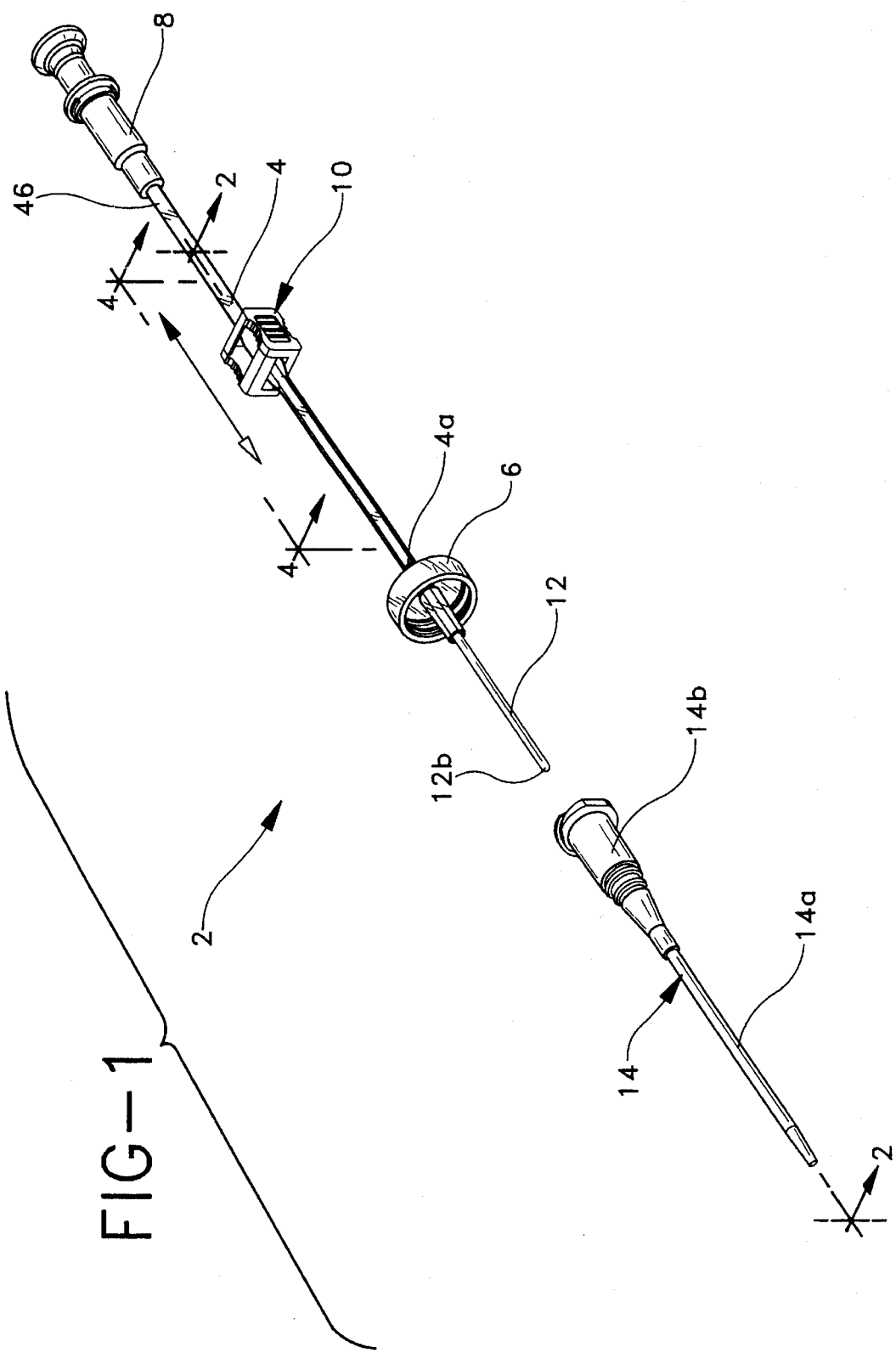
FIG. 1 is a perspective view of the invention.

The following is a description of the preferred embodiment of the invention. It is intended to be illustrative rather than limiting. The full scope of the invention is intended to be determined by reference to the claims.

FIG. 1 shows advancer assembly 2 in perspective view. Advancer assembly 2 is made up of flexible tube 4 having first end 4a and second end 4b. Tube 4 has a cylindrical wall 16 defining a lumen 18 (see FIG. 2). Attached to first end 4a is a male luer connector 6, which in turn allows advancer assembly 2 to be releasably attached to catheter assembly 14. The luer connector may be replaced by a variety of connecting devices, for example a welded or glued connection. Catheter assembly 14 is made up of a conduit in the form of catheter tube 14a and catheter hub 14b. At the second end of tube 4 is female luer connector 8 which enables tube 4 to be connected to peripheral tubing or ports to facilitate the withdrawal or introduction of fluids into the patient via catheter assembly 14.

In FIG. 1, an elongate member 12 in the form of obturator or probe is shown protruding from male luer connector 6. Elongate member could be a probe for sensing physiological parameters such as blood pressure or blood gases or an obturator for selectively occluding catheter tube 14a. Tube 4 is preferably made of PVC. It may be provided with longitudinal reinforcing fibers to limit stretching. Such fibers are neoprene coated glass fibers which are coextruded into tube 4.

Elongate member 12 has a proximal end 12a and a distal end 12b. Secured to proximal end 12a is an object in the form of bead 22. Bead 22 is enclosed within lumen 18 of tube 4 and is confined by surfaces 24 of ribs 20b of advancer 10. Bead 22 is restricted to movement with advancer 10 and cannot move far without the movement of advancer 10. Since bead 22 partially occludes lumen 18, it can be provided with grooves 25 a, b, c, d which facilitate fluid flow through bead 22 (See FIGS. 5a and 5b). If tube 4 is squeezed adjacent bead 27, bead 22 will move axially along lumen 18. If an axial force is imparted to bead 22 through tube 4, bead 22 will likewise move axially along lumen 18.

Advancer 10 is mounted on the outside of tube 4 so that advancer 10 is slidable axially along tube 4. As shown in FIG. 6 advancer 10 is made of two parts 10a and 10b, each of which is provided with a pair of male projections 20a and a pair of female projections in ribs 20b. Ribs 20b are provided with arcuate surfaces 24. Advancer 10 and ribs 20b are dimensioned relative to tube 4 such that when advancer 10 is mounted on the tube as shown in FIG. 1, surfaces 24 squeeze or pinch wall 16 of tube 4, thus reducing the cross sectional area of lumen 18 of tube 4. See FIGS. 2, 3 & 4. The movement of advancer 10 axially along tube 4 progressively pinches tube 4 adjacent bead 22 and thus imparts a substantially axial force to bead 22. This force causes elongate member 12 to be advanced or retracted axially along tube 4 and through catheter tube 14a. Advancer 10 is molded from polystyrene using well known injection molding techniques. Advancer 10 could also be made with rollers replacing ribs 20b. Such rollers are considered to be equivalent to ribs 20b.

In use, advancer assembly 2 is attached to catheter 14 by means of luer connector 6 which mates with luer connector 14b. If elongate member 12 is to be advanced into catheter assembly 14, for example to obturate catheter tube 14a, advancer 10 is slid axially along tube 4. Since the movement of bead 22 and hence elongate member 12 is constrained by surfaces 24 of ribs 20b of advancer 10, elongate member 12 will advance along lumen 18 only as long as advancer 10 slides along tube 4. Similarly elongate member 12 may be withdrawn from catheter 14 by simply sliding advancer from first end 4a towards second end 4b. Ribs 20b squeeze wall 16 of tube 4 around bead 22. The movement of advancer 10 and bead 22 thus resembles a peristaltic movement as bead 22 is advanced along lumen 18 by the squeezing of wall 16. The structure allows the advancement of elongate member 12 into catheter tube 14a without the need for finger contact with elongate member 12 or bead 22, thus maintaining the sterility of elongate member 12.

I claim:

1. A medical device, comprising:

a medical catheter;

an elongate member comprising a proximal end and a distal end;

a flexible tube having a proximal end and a distal end, a lumen and a flexible wall, the flexible tube being dimensioned to accommodate the elongate member axially in the lumen;

connecting means for connecting the distal end of the flexible tube to the catheter;

an object secured to the elongate member such that the elongate member and object are slidably located in the lumen of the flexible tube; and an advancer axially and slidably mounted on the flexible tube such that imparting an axial force to the advancer causes the elongate member and the object to move axially through the lumen toward or away from the proximal end of the flexible tube.

2. The device of claim 1 wherein the object is a bead.

3. The device of claim 1 wherein the object is secured to the second end of the elongate member.

4. The device of claim 1 wherein the advancer comprises means for moving the object axially along the lumen by squeezing the flexible tube, thereby causing part of the wall of the flexible tube to come into contact with the object as the advancer is advanced axially along the tube.

5. The device of claim 1 wherein the means for advancing comprise means for pinching the tube so that part of the tube comes into contact with the object.

6. The device of claim 5 wherein the means for advancing comprise a plurality of opposed ribs and the tube is pinched between the opposed ribs when the advancing means is moved axially along the tube.

7. The device of claim 5 wherein the advancing means comprise a plurality of opposed ribs for progressively pinching the tube when the advancing means is moved in along the tube in the direction of the second end.

8. The device of claim 1 wherein the elongate member is an obturator.

9. The device of claim 1 wherein the elongate member is a probe for detecting a physiological parameter.

10. The device of claim 1 wherein the object is provided with at least one groove to permit fluid flow through the lumen.

11. A medical device, comprising:

an elongate member having a first end and a second end;

a flexible tube having a first end and a second end, a lumen and a flexible wall, the flexible tube being dimensioned to accommodate the elongate member axially in the lumen;

a bead secured to the elongate member and slidably located in the lumen of the flexible tube; and advancing means axially and slidably mounted on the flexible tube such that imparting an axial force to the advancing means causes axial force to be imparted to the bead through the flexible wall of the flexible tube, thereby causing the elongate member to move axially within the lumen.

12. The device of claim 11 wherein the bead is secured to the second end of the elongate member.

13. The device of claim 12 wherein the advancing means comprises means for moving the bead axially along the lumen by squeezing the flexible tube, thereby causing part of the wall of the flexible tube to come into contact with the bead as the advancing means is advanced axially along the tube.

14. The device of claim 12 wherein the means for advancing comprise means for pinching the tube so that part of the tube comes into contact with the bead.

15. The device of claim 12 wherein the means for advancing comprise a plurality of opposed ribs and the tube is pinched between the opposed ribs when the advancing means is moved axially along the tube.

16. The device of claim 12 wherein the advancing means comprise a plurality of opposed ribs for progressively pinching the tube when the advancing means is moved in along the tube in the direction of the second end.

17. The device of claim 11 wherein the elongate member is an obturator.

18. The device of claim 11 wherein the elongate member is a probe for detecting a physiological parameter.

19. The device of claim 11 wherein the bead is provided with at least one groove to permit fluid flow through the lumen.

20. A medical device, comprising:

an elongate member having a first end and a second end;

a flexible tube having a first end and a second end, a lumen and a flexible wall, the flexible tube being dimensioned to accommodate the elongate member axially in the lumen;

connecting means for connecting the first end of the flexible tube to the conduit;

an object secured to the second end of the elongate member such that the elongate member and object are slidably located in the lumen of the flexible tube; and an advancer axially and slidably mounted on the flexible tube such that imparting an axial force to the advancer causes the elongate member and the object to move axially through the lumen toward or away from the second end of the flexible tube.

21. The device of claim 20 wherein the object is a bead.

22. The device of claim 20 wherein the advancer comprises means for moving the object axially along the lumen by squeezing the flexible tube, thereby causing part of the wall of the flexible tube to come into contact with the object as the advancer is advanced axially along the tube.

23. The device of claim 20 wherein the means for advancing comprise means for pinching the tube so that part of the tube comes into contact with the object.

24. The device of claim 23 wherein the means for advancing comprise a plurality of opposed ribs and the tube is pinched between the opposed ribs when the advancing means is moved axially along the tube.

25. The device of claim 23 wherein the advancing means comprise a plurality of opposed ribs for progressively pinching the tube when the advancing means is moved in along the tube in the direction of the second end.

* * * * *

UNITED STATES PATENT AND TRADEMARK OFFICE
CERTIFICATE OF CORRECTION

PATENT NO. : 5,507,728
DATED : April 16, 1996
INVENTOR(S) : Timothy J. Erskine

It is certified that error appears in the above-indentified patent and that said Letters Patent is hereby corrected as shown below:

On the title page, item [54] and column 1, line 2, change "ADVANCES" to --ADVANCER--.

Signed and Sealed this

Twenty-sixth Day of November 1996

Attest:

BRUCE LEHMAN

Attesting Officer

Commissioner of Patents and Trademarks